(12) United States Patent　　(10) Patent No.: US 11,944,556 B2
Michalak　　(45) Date of Patent: Apr. 2, 2024

(54) STENT GRAFT DEVICE WITH ANCHORING MEMBERS HAVING ADJUSTABLE GEOMETRIES

(71) Applicant: W. L. Gore & Associates, Inc., Newark, DE (US)

(72) Inventor: Christopher S. Michalak, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 627 days.

(21) Appl. No.: 16/934,147

(22) Filed: Jul. 21, 2020

(65) Prior Publication Data

US 2020/0345523 A1　　Nov. 5, 2020

Related U.S. Application Data

(63) Continuation of application No. 15/161,569, filed on May 23, 2016, now Pat. No. 10,765,539.
(Continued)

(51) Int. Cl.
*A61F 2/848* (2013.01)
*A61F 2/07* (2013.01)
*A61F 2/844* (2013.01)

(52) U.S. Cl.
CPC ............... *A61F 2/848* (2013.01); *A61F 2/07* (2013.01); *A61F 2/844* (2013.01);
(Continued)

(58) Field of Classification Search
CPC .... A61F 2/07; A61F 2/848; A61F 2002/9505; A61F 2002/9511; A61F 2002/9528; A61F 2002/9534
See application file for complete search history.

(56) References Cited

U.S. PATENT DOCUMENTS

| 5,151,105 A | 9/1992 | Kwan-Gett |
| 8,057,420 B2 | 11/2011 | Meade et al. |

(Continued)

FOREIGN PATENT DOCUMENTS

| AU | 767566 B2 | 11/2003 |
| JP | 2007-537842 A | 12/2007 |

(Continued)

OTHER PUBLICATIONS

International Preliminary Report on Patentability received for PCT Patent Application No. PCT/US2016/033857, dated Dec. 7, 2017, 11 pages.

(Continued)

*Primary Examiner* — Sarah W Aleman

(57) ABSTRACT

A stent graft device that includes a frame, a cover material covering the frame, and an anchoring member having an adjustable geometry is provided. The anchoring member may be incorporated as part of the frame or coupled thereto. The anchoring member may be formed of a material having a tensile strength such that it can be bent, straightened, or otherwise changed in shape. Tissue growth over and/or around the anchoring member anchors the stent graft device within a lumen. During removal of the stent graft device, the geometry of the anchoring member changes to allow the anchoring member to be removed from the tissue growth along a removal path with minimal trauma. The design and/or shape of the anchoring member is not particularly limited so long as the anchoring member has an adjustable geometry that permits tissue overgrowth and subsequent removal from the tissue overgrowth with minimal trauma.

16 Claims, 8 Drawing Sheets

Related U.S. Application Data

(60) Provisional application No. 62/166,756, filed on May 27, 2015.

(52) U.S. Cl.
CPC .............. *A61F 2002/8483* (2013.01); *A61F 2002/8486* (2013.01); *A61F 2220/0008* (2013.01); *A61F 2220/0016* (2013.01); *A61F 2250/0059* (2013.01)

(56) References Cited

U.S. PATENT DOCUMENTS

| | | | |
|---|---|---|---|
| 8,998,973 B2* | 4/2015 | Molaei | A61F 2/07 623/1.13 |
| 10,765,539 B2 | 9/2020 | Michalak | |
| 2007/0093888 A1 | 4/2007 | Thistle et al. | |
| 2009/0187240 A1 | 7/2009 | Clerc et al. | |
| 2012/0172965 A1* | 7/2012 | Kratzberg | A61F 2/9661 623/1.35 |
| 2012/0179086 A1 | 7/2012 | Shank et al. | |
| 2013/0006347 A1* | 1/2013 | McHugo | A61F 2/95 623/1.12 |
| 2013/0018450 A1 | 1/2013 | Hunt | |
| 2013/0245749 A1 | 9/2013 | Sherry | |
| 2014/0277560 A1* | 9/2014 | Walak | A61F 2/848 623/23.7 |
| 2016/0346075 A1 | 12/2016 | Michalak | |

FOREIGN PATENT DOCUMENTS

| | | |
|---|---|---|
| WO | 2000/018322 A1 | 4/2000 |
| WO | 2000/078250 A1 | 12/2000 |
| WO | 2005/112821 A2 | 12/2005 |
| WO | 2009/052188 A1 | 4/2009 |
| WO | 2011/031981 A1 | 3/2011 |

OTHER PUBLICATIONS

International Search Report dated Sep. 8, 2016, for PCT/US2016/033857.
International Written Opinion received for PCT Patent Application No. PCT/US2016/033857, dated Sep. 19, 2016, 9 pages.
Partial International Search Report PCT/US2016/033857 dated Jul. 29, 2016.

\* cited by examiner

STENT GRAFT DEVICE WITH ANCHORING MEMBERS HAVING ADJUSTABLE GEOMETRIES

CROSS-REFERENCE TO RELATED APPLICATION

This application is a continuation of U.S. patent application Ser. No. 15/161,569, filed May 23, 2016, which claims the benefit of U.S. Provisional Application 62/166,756, filed May 27, 2015, both of which are incorporated herein by reference in their entireties for all purposes.

FIELD

The present disclosure relates generally to implantable medical devices, and more specifically, to a stent graft device having an anchoring member with an adjustable geometry that enables atraumatic removal of the stent graft device.

BACKGROUND

A wide variety of known medical devices can be implanted within a patient's body to provide interventional or remedial treatments. Stent graft devices can be implanted in patients to treat various medical conditions or to treat weak points, known as aneurisms, in the vasculature of a patient. For example, stent graft devices are implanted within a patient to treat an aneurysm in a blood vessel. In another example, stent graft devices are implanted within a patient to seal an opening within the wall of a body lumen (e.g., GI tract) or organ. In a further example, stent graft devices are implanted within a patient to treat a body lumen that has a stricture, such that the device opens or enlarges a fluid flow pathway through the body lumen.

Once deployed to the desired position within a patient, the ongoing efficacy of implantable devices can often depend on their ability to remain in an approximately fixed position relative to the surrounding tissue. For example, an occlusion device implanted to occlude or close an aperture should maintain its proper position relative to the tissue surrounding the aperture, or it may fail to close the aperture. Similarly, a stent graft device deployed in the location of a stricture should remain in the location of the lumen stricture to create or enlarge an open passageway for fluid flow.

In addition, it may be desirable for the medical device to be removed once the intended therapy or treatment is completed. Removal of such devices may be difficult due to tissue growth into and around the medical device. Thus, there exists a need in the art for a medical device that can be used in intraluminal or transluminal applications for the fully intended term of therapy and which can be removed with minimal trauma to the surrounding tissue and to the patient once the therapy is complete.

SUMMARY

One embodiment of the invention relates to a stent graft device that includes (1) an expandable frame, (2) a covering extending over the expandable frame, and (3) an anchoring member coupled to the expandable frame and extending along a length of the expandable frame. The anchoring member moves axially with minimal displacement of tissue growth around the anchoring member for removal of the anchoring member from the expandable frame. In at least one embodiment, the anchoring member has a generally serpentine or a "cork-screw" configuration. The anchoring member may be coupled to the expandable frame by a plurality of coupling members (e.g., loops) positioned on an exterior surface of the expandable frame. A mechanical force may be applied to one end of the anchoring member to disengage the anchoring member from the overgrown tissue and move the anchoring member along a removal path that is defined along the length of the stent by the anchoring member with minimal to no trauma to the tissue. The geometry of the anchoring member changes for removal of the anchoring member from tissue growth along the removal path.

A second embodiment of the invention relates to a stent graft device that includes (1) an expandable frame, (2) a covering extending over the expandable frame, and (3) at least one anchoring member coupled to the exterior of the expandable frame. The anchoring members may be coupled to the stent at discrete, spaced apart locations. The coupling members form raised portions that extend away from the frame, and may have a generally "u"-shaped or curved configuration. The geometry of the anchoring member defines a removal path for the anchoring member. Each anchoring member extends a distance along the expandable frame in an implanted state. The anchoring member is adapted for removal from tissue overgrowth along the removal path of the anchoring member. Tissue overgrowth on and/or around the anchoring member anchors the stent graft device within a lumen. Removal of the anchoring member from the overgrown tissue is atraumatic. The anchoring member may be coupled to the expandable frame at an attachment region located on an exterior surface of the expandable frame.

A third embodiment of the invention relates to a stent graft device that includes (1) an expandable support frame having incorporated therein an anchoring member to anchor the stent graft device in a lumen and (2) a covering extending over the expandable support frame. In one embodiment, the anchoring member is a coiled wire extending outwardly from the expandable support frame. The geometry of the anchoring member changes for removal of the anchoring member from tissue growth around the anchoring member. For example, the anchoring member assumes an uncoiled configuration for removal of the anchoring member from tissue overgrowth and subsequent removal of the stent graft device from the lumen. In another embodiment, the anchoring member includes a first member and an opposing second member such that the first member and the second member are engaged with each other in an implanted state. The first and second members disengage for removal of the stent graft device from the lumen. The geometry of the engaged first and second members change to a disengaged configuration for removal of the anchoring member from the tissue overgrowth. The anchoring members are removed from tissue overgrowth along a removal path defined by the geometry of the anchoring member. The tissue overgrowth on the anchoring members anchors the stent graft device in the lumen.

A fourth embodiment of the invention relates to a method for removing a stent graft device from a lumen that includes (1) providing a stent graft device having an expandable frame and an anchoring member coupled thereto and (2) applying a mechanical force to the anchoring member to remove the anchoring member from the stent graft device along a removal path. The anchoring member extends along a length of the expandable frame and defines the removal path of the anchoring member. The expandable frame has a cover extending over the expandable frame. The anchoring member is coupled to the frame by a coupling member, such as via loops, positioned on the exterior surface of the expandable frame. Once the anchoring member is decoupled and removed from the stent graft device, the stent graft device may be removed from the lumen.

A fifth embodiment of the invention relates to a method of removing a stent graft device from a lumen that includes (1) providing a stent graft device having incorporated therein an anchoring member extending outwardly from the stent graft device and (2) applying a mechanical force to change a geometry of the anchoring member to remove the anchoring member along a removal path defined by the anchoring member. The stent graft device includes an expandable support frame having the anchoring member incorporated therein and a covering extending over the expandable support frame. In one embodiment, the anchoring member has a coiled configuration and changing the geometry includes uncoiling the anchoring member. In a further embodiment, the anchoring member includes a first member and an opposing second member such that the first member and the second member are engaged with each other. In this embodiment, changing the geometry includes disengaging the first member and the second member. Once the anchoring member has been disengaged and/or removed from the tissue overgrowth, the stent graft device may be removed from the lumen.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

GLOSSARY

Figure 1:
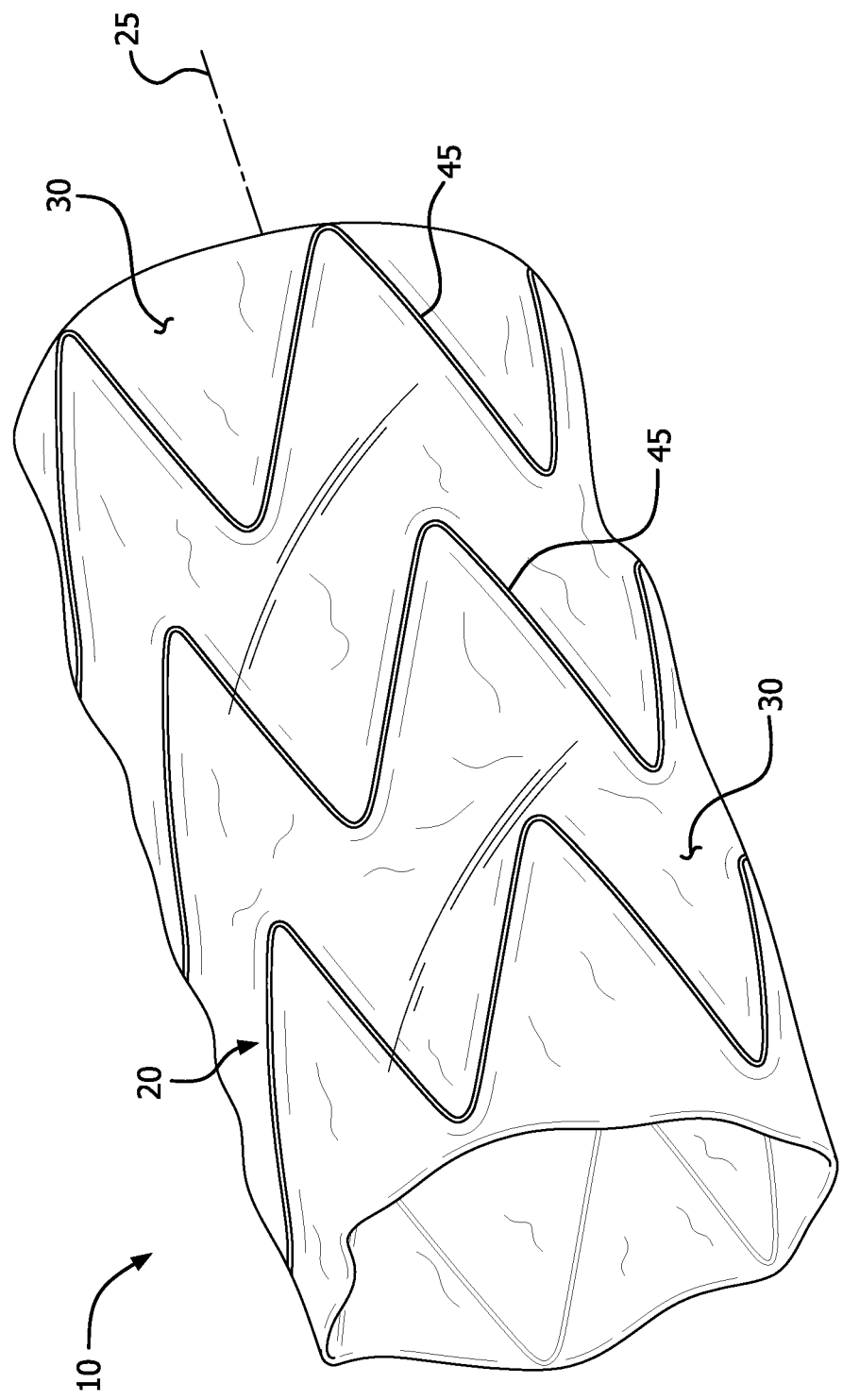
FIG. 1 is a schematic illustration of a stent graft device according to at least one embodiment of the invention.

The terms "tissue growth" and "tissue overgrowth" as used herein are meant to include any tissue that is attached or adhered to, positioned within, located around, is touching, or is otherwise in contact with an anchoring member that anchors the medical device in any portion of a lumen or translumenally.

The term "adjustable geometry" as used herein is meant to denote that the shape of the anchoring member or the anchoring member's position with respect to the stent changes to permit removal of the anchoring member from tissue overgrowth.

The term "macroscopic" as used herein is meant to denote that the tissue overgrowth is on a cellular level.

The term "atraumatic" as used herein is meant to denote minimal or no tissue injury as a result of removing the anchoring member from overgrown tissue.

The term "minimal trauma" as used herein is meant to describe a degree that will not induce a negative consequence to the patient.

As used herein, the term "lumen" is meant to denote the inside of a tubular structure such as an artery, intestine, duct or tract.

DETAILED DESCRIPTION

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting. It is to be understood that the terms "stent graft device" and "stent" are used interchangeably herein. It is also to be understood that the terms "frame" and "stent frame" are used interchangeably herein.

The present invention is directed to a stent graft device that includes a frame, a cover material covering the frame, and at least one anchoring member coupled to or integrated into the frame. Tissue growth over and/or around the anchoring member anchors the stent graft device within a lumen. The geometry of the anchoring member changes to allow the anchoring member to be removed from the tissue growth with minimal trauma. It is to be appreciated that the stent graft devices and anchoring members described herein are scalable to a broad range of sizes and geometries so that the stents and anchoring members can be used in a wide variety of different anatomies, implant sites (e.g., body lumens, organs, and cavities), and types of implementations.

It is to be noted that although the invention is described herein with reference to stent graft devices, it is to be appreciated that any medical device containing a cover material and an anchoring member that can be geometrically altered for atraumatic removal of the stent from a lumen may be used and is considered to be within the purview of the invention.

Turning to FIG. 1, a schematic illustration of an exemplary stent graft device is depicted. The stent graft device 10 may be used in intraluminal or transluminal applications. The stent graft device 10 includes a stent frame 20 and a covering material 30. The stent graft device 10 is generally cylindrical and defines a longitudinal axis 25. In some embodiments, the ends of the stent graft device 10 may be scalloped or contoured to the shape of the stent frame. Additionally, one or more fenestrations and/or side branches may be included in the stent graft device 10. The stent graft device 10 provides an apposition force to the lumen such that anchoring members, described in detail hereafter, are brought into contact with the tissue of the body lumen to allow for tissue growth over and/or around the anchoring members.

The frame 20 may be formed of one or more elongate member (e.g., a wire) that has been helically wrapped into a tubular form. In exemplary embodiments, the stent frame 20 is formed of a single helically wound elongate member. In the embodiment depicted in FIG. 1, the elongate member is wrapped about a tubular member such that each stent ring 45 within the frame 20 has a generally serpentine shape (e.g., a sinusoidal shape or a zig-zag form). It should be understood, however, that the depicted stent frame 20 is not the only stent frame configuration envisioned within the scope of this invention. The stent frame 20 can differ from the embodiment depicted in FIG. 1 in numerous ways such as, but not limited to, the number of stent rings, the shape of the stent rings, the diameter of the stent rings, the geometry of the stent rings, the pitch of the stent rings, the number of wires, and/or the diameter of the wire (e.g., the elongate member). For instance, the elongate member may be wrapped so as to form other geometries, and such other geometries are considered to be within the purview of the invention. In other embodiments, some or all of the stent frame 20 is formed of stent rings that have interconnecting elements. Additionally, the stent frame 20 may be formed of braided or interwoven elongate members.

In an alternate embodiment, the frame 20 is formed from a tube or sheet of a material that is cut according to a pattern and then expanded (and in some embodiments heat-set). For example, frame 20 may be fashioned from a tubular material to form rings and/or cellular/lattice structures. In some embodiments, the frame is cut from a sheet of material that is then formed into a ring or tubular cellular structure. Such cutting may be performed by laser cutting, chemical etching, machining, or water-jet cutting. In at least one embodiment, some or all of the stent frame 20 has a cellular construct.

The stent frame 20 may be formed of various materials and/or combinations of materials. In exemplary embodiments, nitinol (NiTi) is used as the material of the stent frame 20. Other materials such as stainless steel, polymeric materials, polyamide, polyester, polyimide, biosorbable polymers, a cobolt, chromium, nickel alloy, or any other appropriate biocompatible material, and combinations thereof, may be used as the material of the stent frame 20. The stent frame 20 is generally conformable, fatigue resistant, elastic, and distensible such that the stent frame 20 can conform to the topography of the surrounding tissue when the stent graft device 10 is deployed in a lumen.

The stent frame 20 provides structure and shape for the stent graft device 10. In the embodiment depicted in FIG. 1, the covering material 30 is attached to the stent frame 20 to create a tubular fluid conduit. The stent frame 20 thereby provides a supportive structural framework for the covering material 30 that may otherwise be relatively flaccid and flexible. The covering material 30 is attached to at least a portion of the outer surface of the stent frame 20. "Outer portion" as used herein is meant to denote the surface of the covering material 30 that faces, and is optionally in contact with, the wall of the lumen. In some embodiments, the covering material 30 is attached to the frame 20 with an adhesive material, such as, for example, a silicone, a polyurethane, or fluorinated ethylene propylene (FEP). Silicone, for example, acts as a bonding agent to adhere the covering material 30 to the stent frame 20. The adhesive material may be applied to portions of the stent frame 20 or to all of the stent frame 20.

In one or more embodiment, some or all of the covering material 30 is disposed on both the inner portion and on the outer portion of the stent frame 20 and the portions of the covering material 30 are adhered to each other so as to encapsulate portions of or the entirety of the stent frame 20. Stitching, lashing, banding, and/or clips may be alternatively used to attach the covering material 30 to the stent frame 20. In some embodiments, a combination of techniques is used to attach the covering material 30 to the stent frame 20.

The cover material 30 may be formed of a membranous material that inhibits or reduces the passage of blood, bile, and other bodily fluids and materials through the covering material 30. In an exemplary embodiment, the cover material 30 is a polymer material, such as, for example, a fluoropolymer material. In at least one embodiment, the cover material 30 is an expanded polytetrafluoroethylene membrane. It is to be appreciated that the cover material 30 may be formed of other materials, such as, but not limited to a silicone, a urethane, a polyester (e.g., DACRON®), and combinations thereof.

The stent graft device 10 may be delivered to, and deployed at, an in vivo deployment site using various minimally invasive transcatheter deployment techniques. In such an embodiment, the stents 10 may have a delivery configuration and a deployed configuration. For example, while the stent is being delivered to the deployment site within a delivery sheath, the stent may be configured in a collapsed, low-profile delivery configuration within a delivery sheath. After emergence of the stent from the delivery sheath, the stent may assume an expanded or deployed configuration. In some embodiments, the stent may self-expand to the expanded or deployed configuration. In other embodiments, the stent may expand in response to the application of supplemental force from another device (e.g., a dilation balloon). In some embodiments, a combination of self-expansion and forced expansion may be used to expand the stent to its deployed configuration. The stent may be implanted, for example, in a patient in the location of a lumen stricture to create or enlarge an open passageway for fluid flow. In some embodiments, the stent may be dilated with extrinsic force beyond its nominal diameter for therapy. Once therapy is completed, the stent will return to its nominal diameter with the removal of the extrinsic force.

It is to be understood that the stent graft device may expand in conformance to the topography of the surrounding tissue when the devices are implanted within a patient. As a result, the in situ deployed configuration of the stent graft devices may or may not be the fully expanded configuration of the devices. That is, while the stent graft device is deployed, the stent may assume one or more partially expanded or partially deployed configurations to enable at least the anchoring members of the stent graft device to be in contact with body tissue.

As mentioned previously, the stent graft device 10 also contains at least one anchoring member that may be incorporated as part of the frame 20 or coupled to the frame 20. The design and/or shape of the anchoring member is not particularly limited so long as the anchoring member has an adjustable geometry that perm its tissue overgrowth and subsequent removal from the tissue overgrowth with minimal trauma. It is to be appreciated that tissue overgrowth and tissue growth, as used herein, may include any tissue that is attached or adhered to, positioned within, located around, is touching, or is otherwise in contact with an anchoring member that anchors the stent graft device in any portion of the lumen or translumenally. The anchoring member may be formed of a material having a tensile strength such that it can be bent, straightened, or otherwise changed in shape. Non-limiting examples of suitable materials for use as an anchoring member include, but are not limited to, nitinol wire, Platinol™, cobalt chromium, various stainless steel alloys, polypropylene, polyamides, and/or other implantable metal or polymeric materials.

Figure 2:
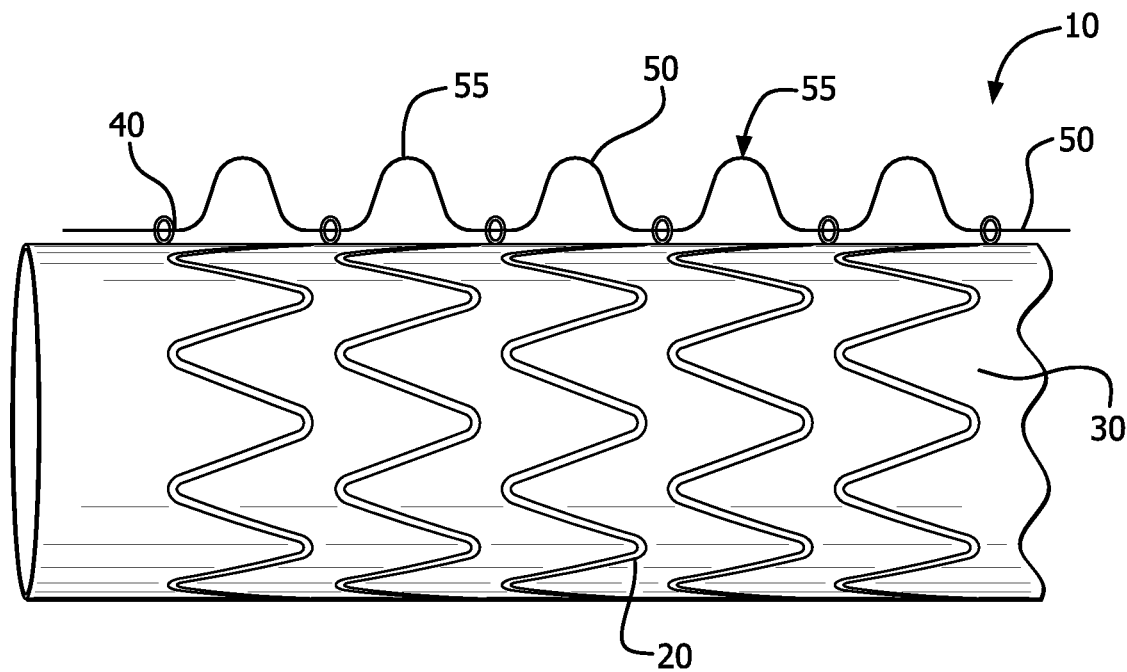
FIG. 2 is a schematic illustration of a stent graft device having an anchoring member extending along the length of the stent graft device according to an embodiment of the invention.
Figure 3A:
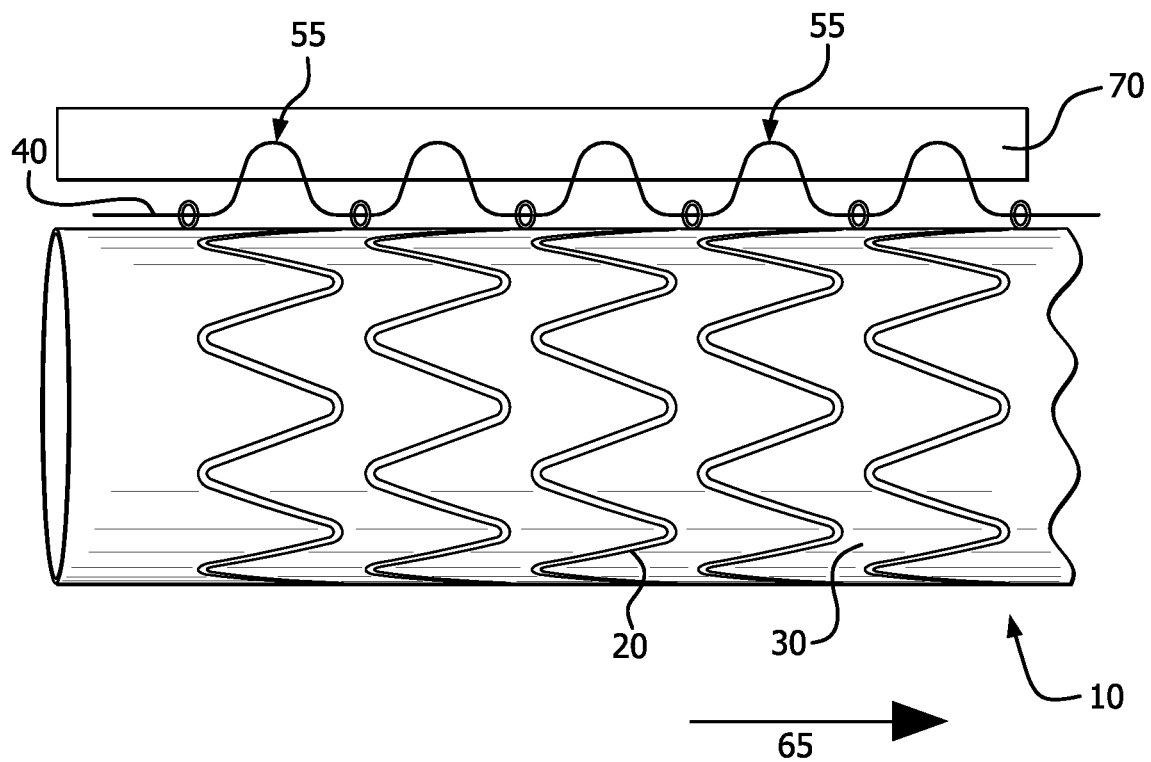
FIG. 3A is a schematic illustration of tissue overgrowth embedding the raised portions of the anchoring member of FIG. 2 in a lumen wall according to an embodiment of the invention.

FIG. 2 is a schematic illustration of an exemplary anchoring member 50 extending along the length of the stent graft device 10. The anchoring member 50 may extend along the entire length or may extend along a portion of the stent graft device 10. The stent graft device 10 may have, either integrated into the frame 20 or coupled to the frame 20, coupling members 40 (e.g., loops) through which the anchoring member 50 is threaded. It is to be appreciated that the coupling members 40 depicted in FIG. 2 are exemplary in nature and may have any shape or design may be utilized as long as it is capable of being threaded therethrough with the anchoring member 50. The anchoring member 50 may have a configuration (e.g., a serpentine or a cork-screw configuration) that forms raised portions 55 between successive coupling members 40. In exemplary embodiments, the raised portions 55 are in contact with the inner surface of a body lumen 70. As shown in FIG. 3A, tissue may grow over and/or around the anchoring member 50, especially at the raised portions 55, to embed the anchoring member 50 in the lumen wall 70. The tissue overgrowth on the anchoring member 50 anchors and/or helps to anchor, the stent graft device 10 within a lumen.

To remove the anchoring member 50 from the overgrown tissue, a mechanical (e.g., longitudinal) force may be applied to one end of the anchoring member 50 to disengage the anchoring member 50 from the overgrown tissue and move the anchoring member 50 along a removal path defined by the geometry of the anchoring member along the length of the stent 10 with minimal to no trauma to the tissue. For example, one end of the anchoring member 50 may be grasped and pulled to not only disengage the anchoring member 50 from the tissue but also to pull the anchoring member 50 along the removal path. The stent graft device 10, absent the anchoring member 50, may then be removed by any conventional method.

Figure 3B:
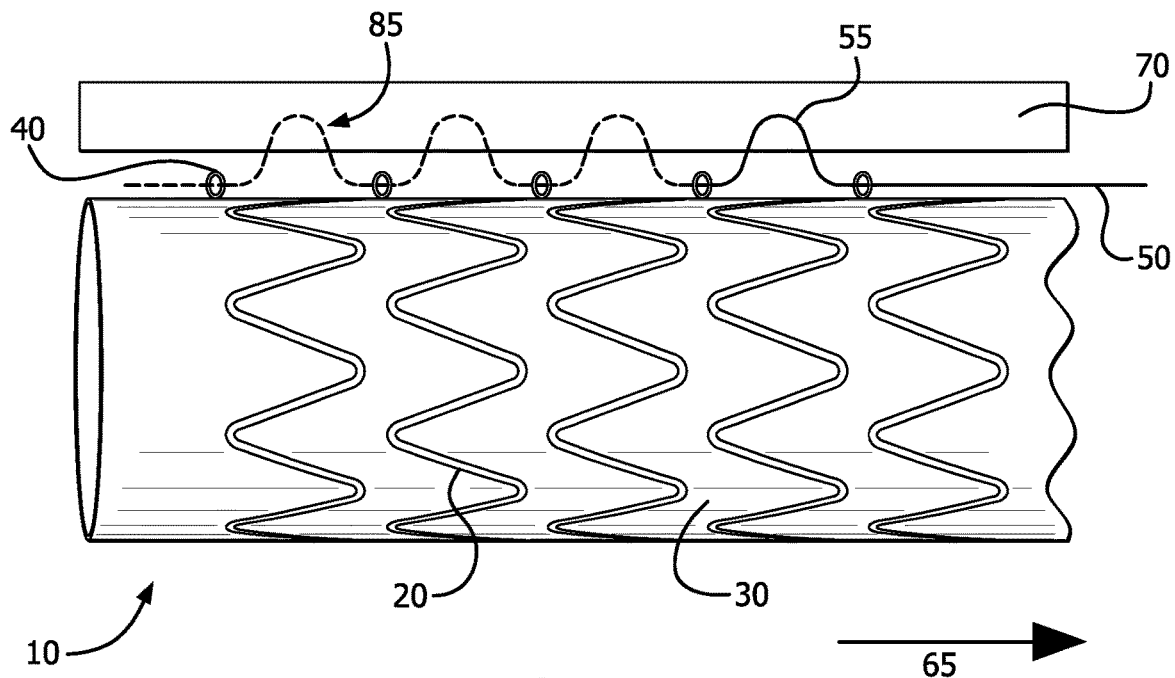
FIG. 3B is a schematic illustration of the removal of the anchoring member of FIG. 3A from the overgrown tissue along a removal path in accordance with at least one embodiment of the invention.

The removal of the anchoring member 50 is schematically shown in FIGS. 3A and 3B. As shown in FIG. 3A, tissue overgrowth may embed the raised portions 55 of the anchoring member 50 in the lumen wall 70. To remove the anchoring member 50, the anchoring member 50 may be pulled in the direction of arrow 65. When pulled, the anchoring member 50 moves axially with minimal displacement within the encapsulated tissue along the removal path 85 formed by the anchoring member 50 to remove the anchoring member from the expandable frame 20, as shown schematically in FIG. 3B. During removal, the geometry (i.e., shape) of the anchoring member 50 changes so that the anchoring member 50 can follow the removal path 85 with minimal tissue trauma the surrounding tissue.

Figure 4A:
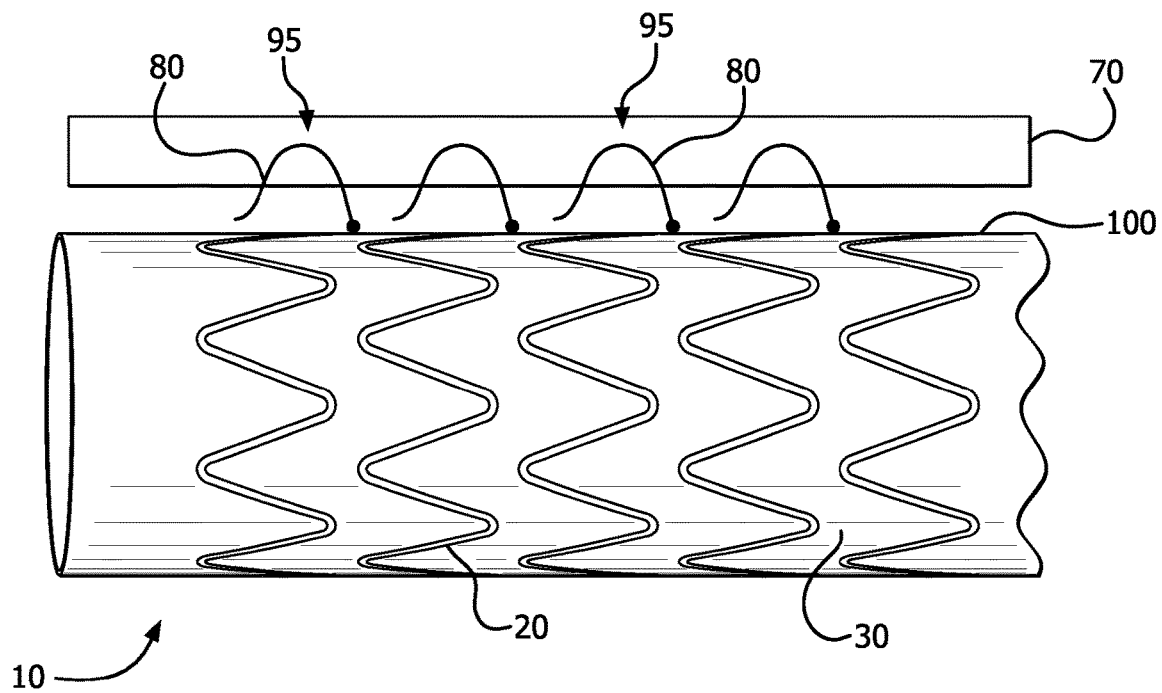
FIG. 4A is a schematic illustration of a stent graft device having a plurality of anchoring members attached at one end thereof to the stent frame at discrete, spaced apart locations according to at least one embodiment of the invention.

In another exemplary embodiment, depicted generally in FIG. 4A, the stent graft device 10 has a plurality of anchoring members 80 coupled to the stent frame 20 at discrete, spaced apart locations. The attachment regions of the anchoring members 80 to the stent frame 20 are identified by reference numeral 100. Each anchoring member extends along a length of the expandable frame in an implanted state. The anchoring members 80 are attached to the frame 20 at one end thereof and form raised portions 95 that extend from the frame 20. The raised portions 95 of the anchoring members 80 depicted in FIG. 4A are exemplary in nature, and it is to be appreciated that the anchoring members 80 may have alternate shapes, lengths, and/or dimensions so long as tissue overgrowth may occur on at least a portion of the anchoring member 80 to at least temporarily embed the anchoring member 80 in the lumen 70 wall. For example, the anchoring members 80 may have a less rounded configuration or contain more than one raised region (not illustrated). Similar to the embodiment depicted in FIG. 2, tissue growth occurs over and/or around the anchoring members 80 in the raised portions 95 to anchor the stent graft device 10 within the lumen 70.

Figure 4B:
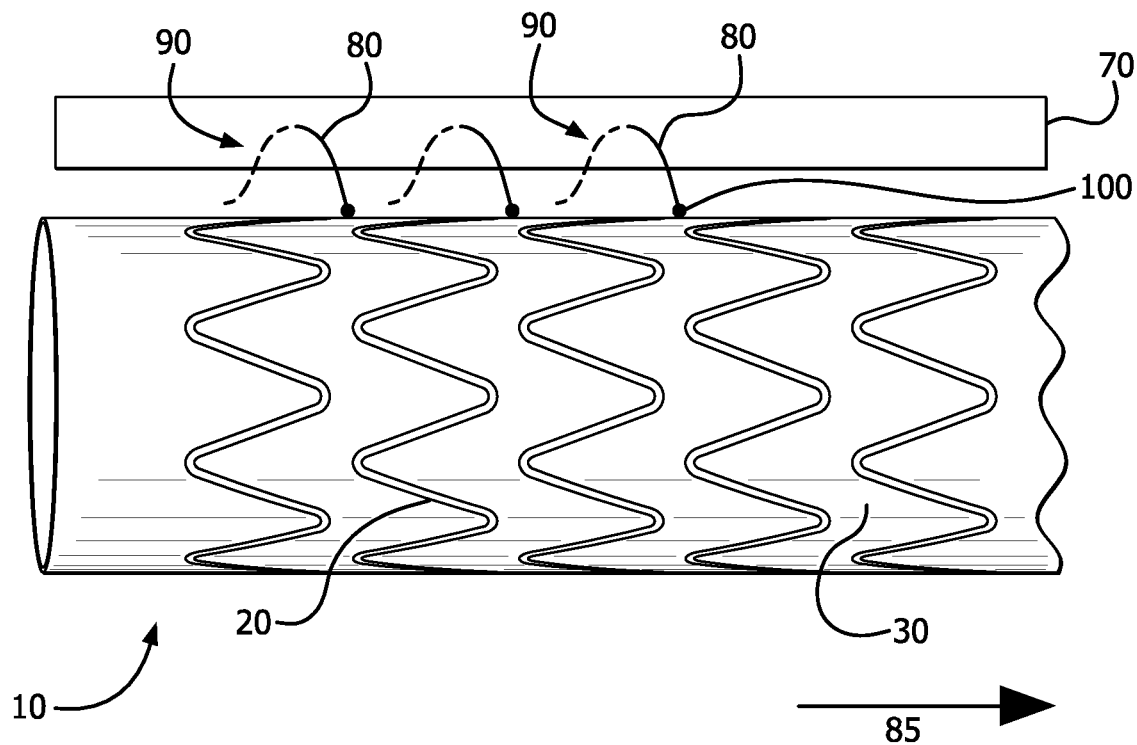
FIG. 4B is a schematic illustration of the removal of the anchoring members of FIG. 4A along a removal path according to at least one embodiment of the invention.

Turning to FIG. 4B, the anchoring members 80 may be atraumatically removed by applying a longitudinal force to the stent graft device 10, such as in the direction of arrow 85. As force is applied to the stent graft device 10, the anchoring members 80 are pulled through the tissue growth along a removal path 90 defined by the anchoring members 80 with minimal displacement of, and trauma, to the overgrown tissue. The anchoring members 80 change geometry (i.e., shape) as the stent graft device 10 is removed so that the anchoring members 80 can follow the removal path 90 with minimal trauma the surrounding tissue.

Figure 5:
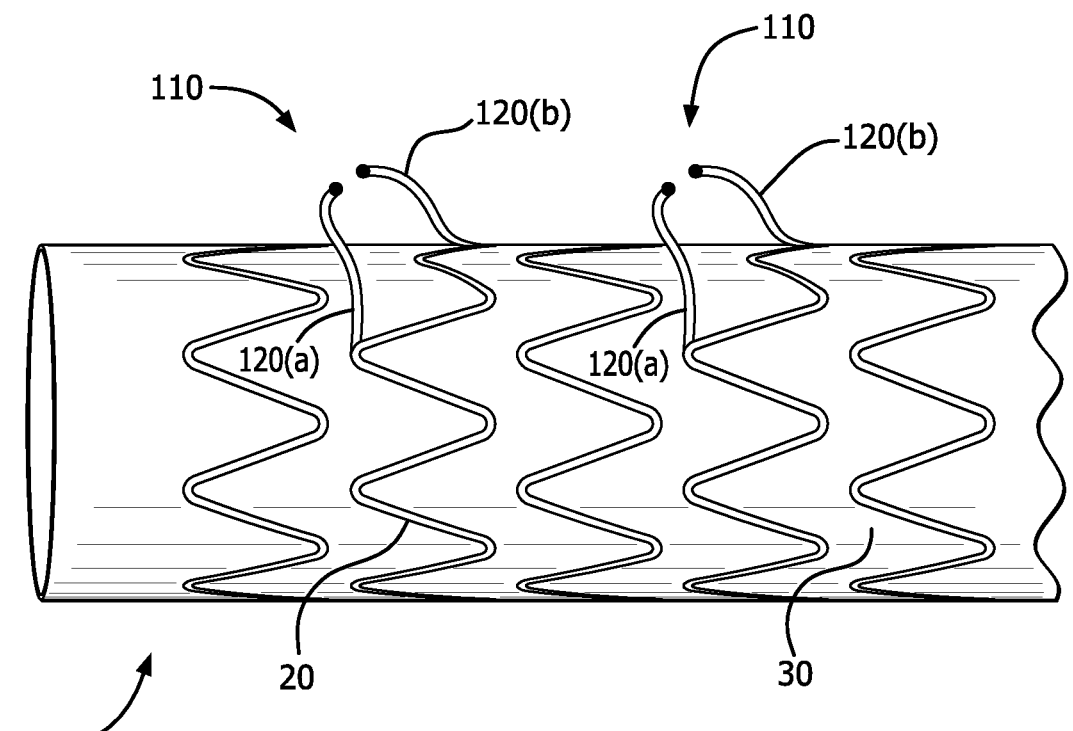
FIG. 5 is a schematic illustration of an anchoring member in the form of opposing fins integrated into the stent frame in accordance with at least one embodiment of the invention.
Figure 5A:
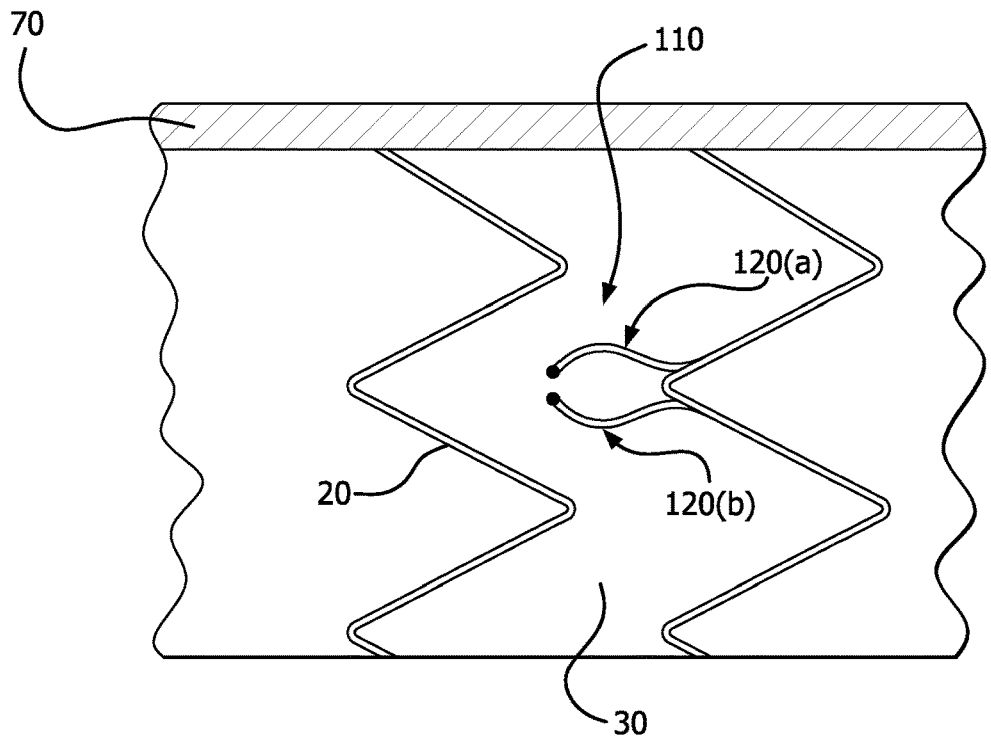
FIG. 5A is a schematic illustration of a top view of the anchoring member of FIG. 5.
Figure 5B:
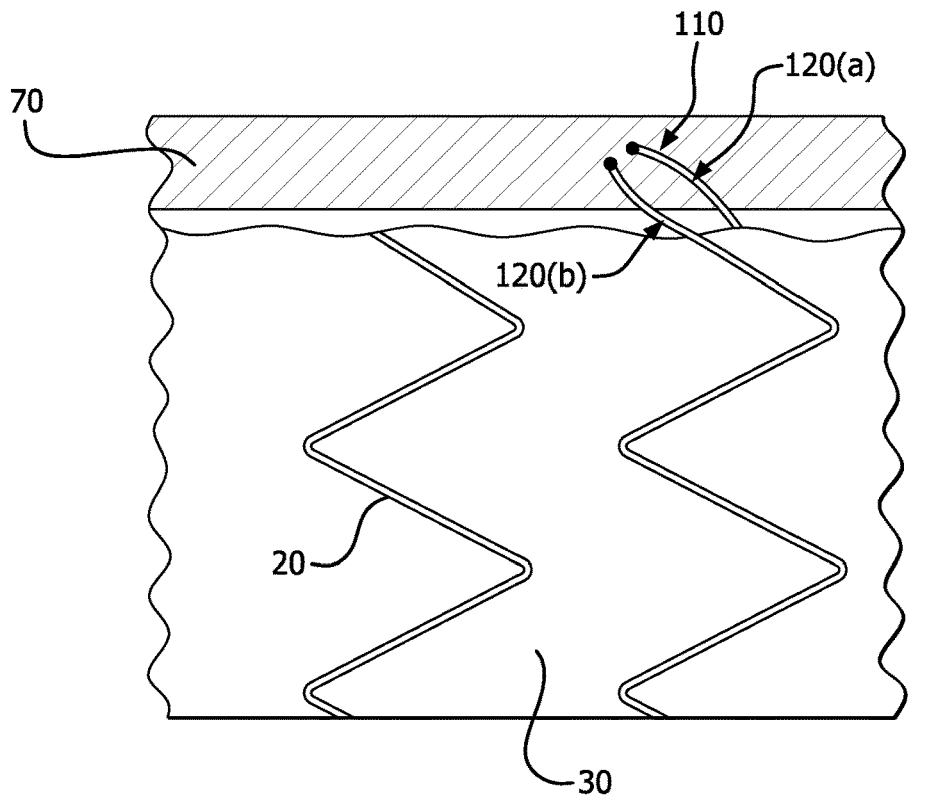
FIG. 5B is a schematic illustration of tissue overgrowth embedding the raised portions of the anchoring member of FIG. 5 in a lumen wall according to an embodiment of the invention.
Figure 5C:
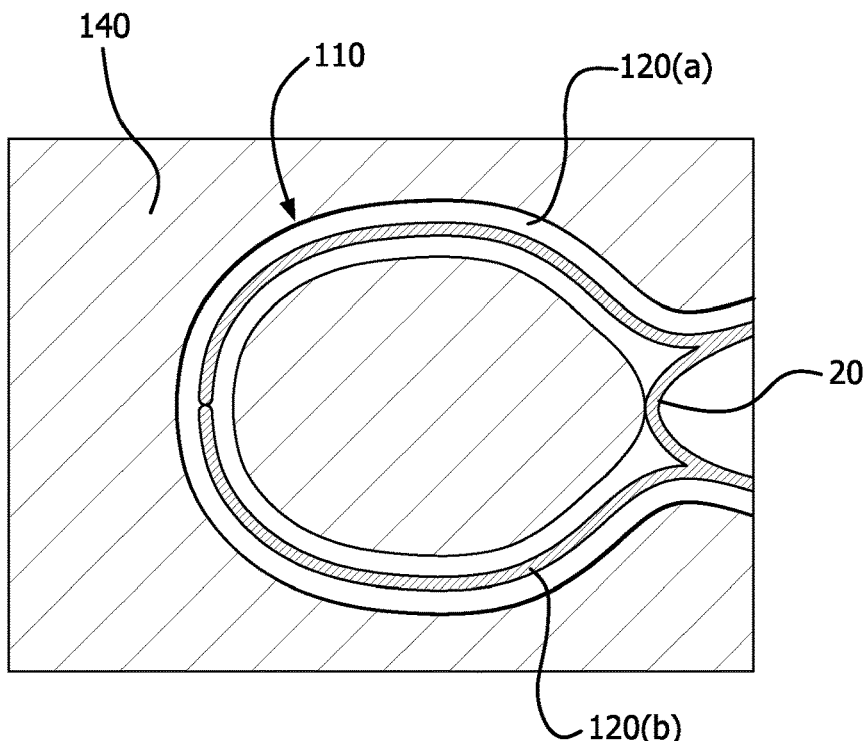
FIG. 5C is a schematic illustration of an anchoring member of FIG. 5 in an engaged configuration in accordance with one exemplary embodiment of the invention.

A further embodiment of an exemplary anchoring member is shown in FIG. 5. In this embodiment, the anchoring member 110 takes the form of opposing fins 120(a), 120(b) that are integrated into the frame 20 of the stent graft device 10. In an alternate embodiment, the anchoring member 110 may be coupled to the frame 20 via a coupling member (not shown). In addition, the fins 120(a) and 120(b) may be formed to be substantial mirror images of each other. The fins 120(a), 120(b) extend away from the frame 20 and are engaged with each other in an implanted state. For example, fin 120(a) and fin 120(b) may be formed such that in an engaged, implanted state they form a raised portion extending outwardly and angularly from the frame 20. The angle at which the fins 120(a), 120(b) extend from the frame 20 may be as great as 90°, and may range from about 10° to about 90°, from about 20° to about 80°, or from about 30° to about 70°. It is to be appreciated that the angle of the fins 120(a), 120(b) with respect to the stent graft device 10 is not particularly limiting so long as tissue is able to grow around and/or over the fins 120(a), 120(b) to anchor the stent graft device 10 within the lumen. A top view showing the positioning of the anchoring member 110 is schematically depicted in FIG. 5A. Tissue grows over and/or around the fins 120(a), 120(b) as depicted generally in FIG. 5B. FIG. 5C depicts an enlarged view of the anchoring member 110 showing fins 120(a), 120(b) in an engaged configuration and overgrown with tissue 140. It is to be appreciated that fins 120(*a*), 120(*b*) are exemplary in nature and may have alternate shapes, lengths, and/or dimensions so long as tissue overgrowth may occur on at least a portion of the anchoring member 80 and the geometry of the anchoring member changes for atraumatic removal along a removal path.

Figure 5D:
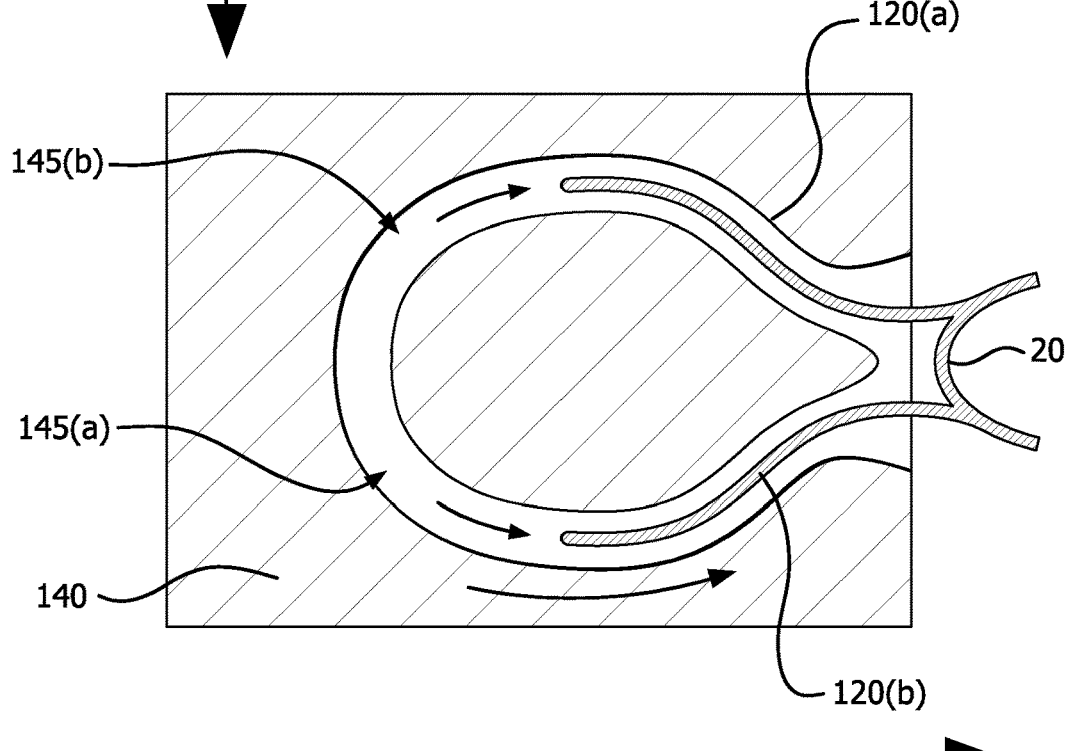
FIG. 5D is a schematic illustration of the removal of an anchoring member of FIG. 5 along removal paths of the fins according to at least one embodiment of the invention.

To remove the stent graft device 10 from the tissue overgrowth 140, a mechanical (e.g., longitudinal) force may be applied to the stent graft device 10, such as in the direction of arrow 130. Pulling or otherwise moving the stent graft device 10 disengages the opposing fins 120(*a*), 120(*b*) of the anchoring member 110, which then move through the overgrown tissue 140 along removal paths 145(*a*) and 145(*b*) defined by the geometry of the fins 120(*a*), 120(*b*), respectively, with minimal displacement of the tissue 140, as shown generally in FIG. 5D. Once the fins 120(*a*), 120(*b*) are disengaged from overgrown tissue 140, the stent graft device 10 may then be removed by any conventional method.

Figure 6:
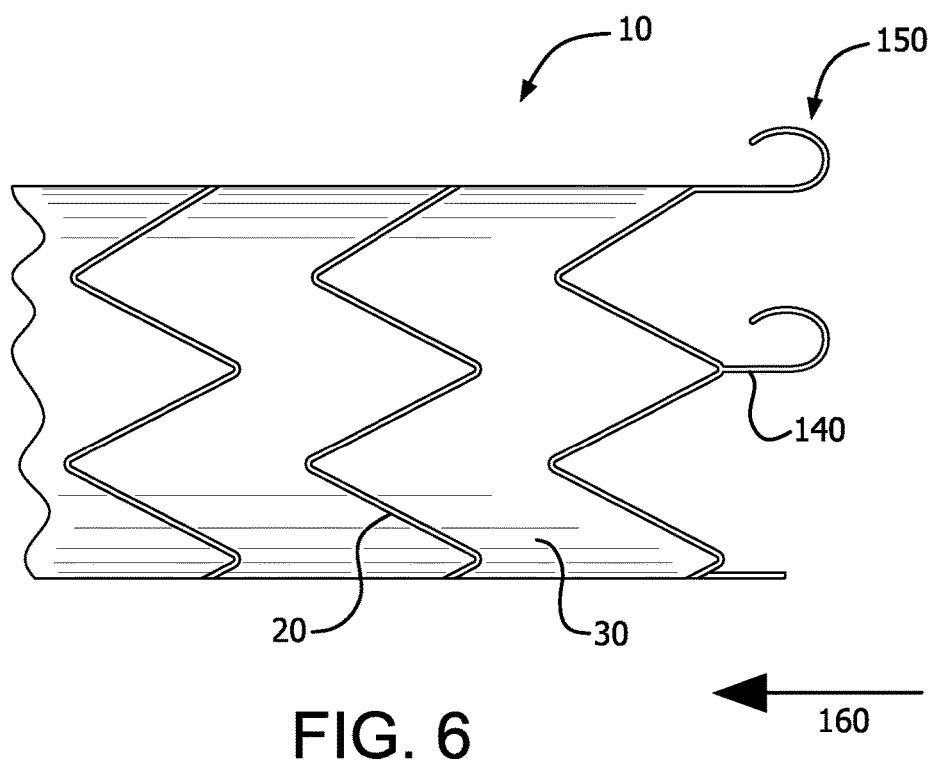
FIG. 6 is a schematic illustration of a stent graft device containing anchoring members in the form of flexible, coiled wires according to an embodiment of the invention.
Figure 6A:
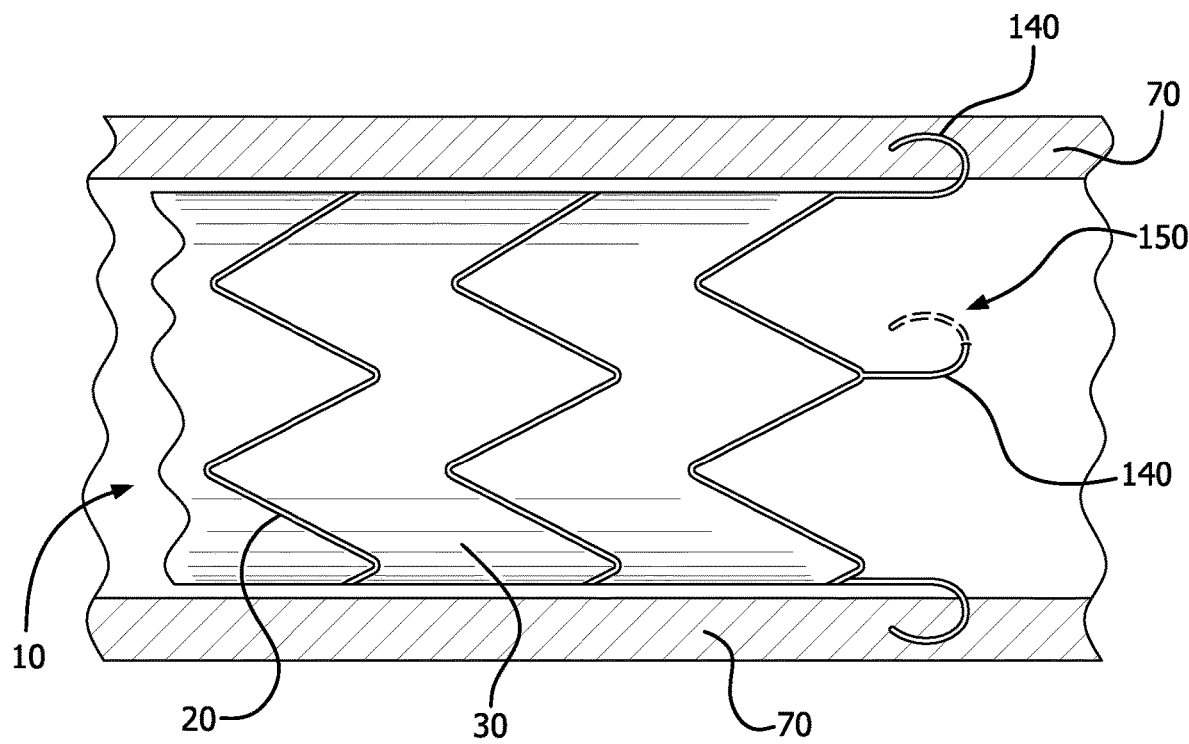
FIG. 6A is a schematic illustration of the stent graft device of FIG. 6 with the anchoring members embedded in tissue overgrowth.
Figure 6B:
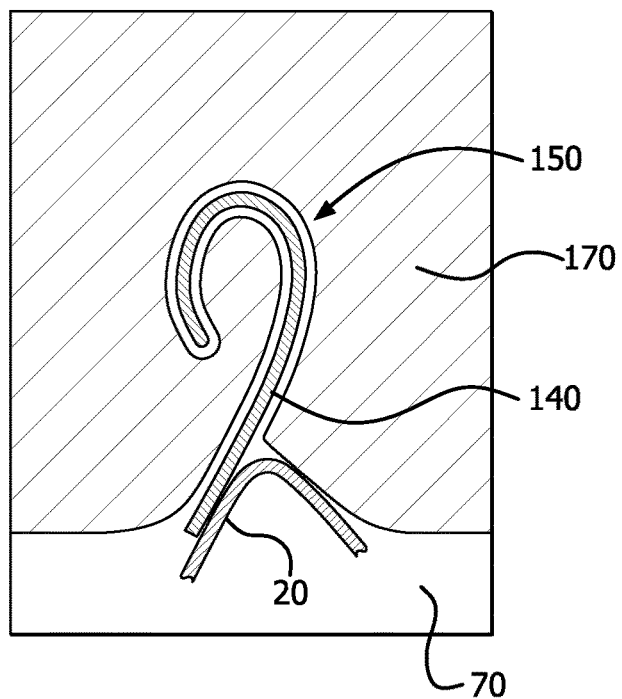
FIG. 6B is an enlarged schematic illustration of an anchoring member of FIG. 6 embedded in tissue overgrowth in accordance with an embodiment of the invention.
Figure 6C:
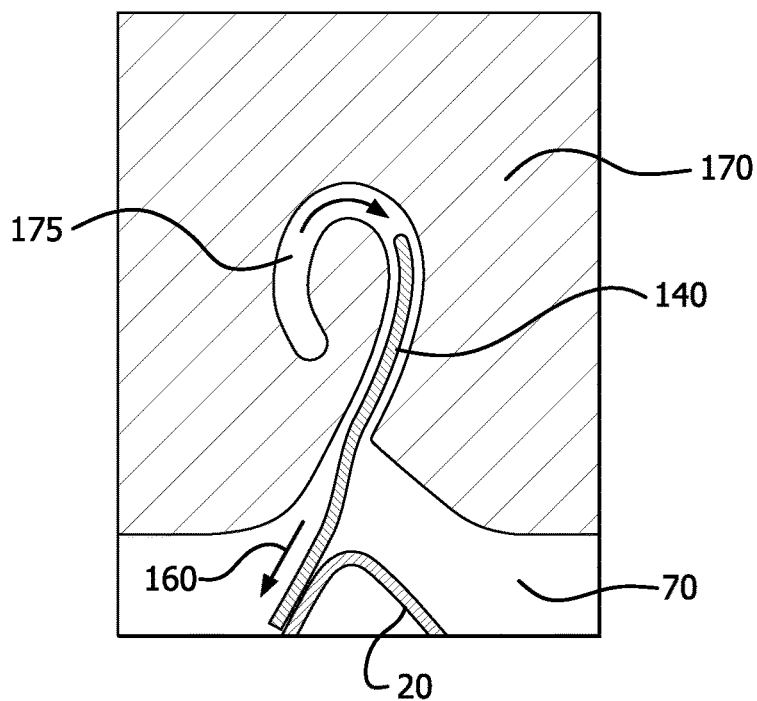
FIG. 6C is an enlarged schematic illustration of the removal of the anchoring member of FIG. 6B along a removal path according to at least one embodiment of the invention.

FIG. 6 is a schematic illustration depicting yet another exemplary anchoring member. As shown in FIG. 6, the stent graft device 10 contains a plurality of anchoring members 140 in the form of flexible, coiled wires that extend away from the frame 20. The anchoring members 140 may be positioned on at least one end of the stent graft device 10. In an implanted configuration, shown generally in FIG. 6A, the anchoring members 150 engage a lumen wall 70 and tissue growth occurs over and/or around the coils 150 of the anchoring members 140, which secures the stent graft device 10 in the lumen 70 until it is time for the stent graft device 10 to be removed. As longitudinal force is applied to the stent graft device 10 in the direction of arrow 160, the anchoring members 140 uncoil and are pulled through the tissue overgrowth along a removal path defined by the geometry of the anchoring members 140 with minimal displacement of the overgrown tissue. An enlarged schematic view of the anchoring member 10 embedded in tissue overgrowth 170 is depicted in FIG. 6B. As the anchoring member 140 is moved in the direction of arrow 160, the anchoring members 140 change geometry (e.g., uncoil or otherwise straighten) as the stent graft device 10 is removed. As depicted in FIG. 6C, the anchoring members 140 follow the removal path 175 to disengage with the surrounding tissue 170. The stent graft device 10 may then be removed by any conventional method.

The radial force provided by the stent frame temporarily anchors and/or holds the stent graft device in place within the lumen so that migration of the stent graft device does not occur upon deployment of the stent graft device. In at least one embodiment, the stent graft device includes a bioabsorbable fixation member (e.g., a hook, barb, suture, or clips) to temporarily anchor and/or hold the stent graft device in place within the lumen so that migration of the stent graft device does not occur upon deployment of the stent graft device. Once sufficient tissue growth over and/or around the anchor member has occurred, tissue growth anchors, and/or helps to anchor the stent graft device within the lumen until the time it is to be removed.

In some embodiments, the stent graft device 10 can be pulled into a retrieval sheath (not shown) once the tissue overgrowth has been disengaged from the anchoring member(s). As the grasping device is further retracted, the entire stent graft device 10 can be pulled into the lumen of the retrieval sheath. Then the retrieval sheath containing the stent graft device 10 can be removed from the patient.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A stent graft device comprising:
   an expandable support frame including an anchoring member that is configured to adopt a shape when the expandable support frame is in an expanded configuration to anchor said stent graft device in a lumen, the shape defining a removal path; and
   a covering extending over said expandable support frame, said anchoring member being removable along said removal path, wherein said anchoring member has a first end and a second end, and is configured such that a geometry of said anchoring member is adapted to change to facilitate the removal of said anchoring member from tissue growth over said anchoring member, the anchoring member configured to be removed along the removal path while the expandable frame is in the expanded configuration such that one of the first and second ends traverses the removal path, wherein the anchoring member is coupled to a coupling member so that at least one or more portions of the anchoring member are spaced apart from the expandable support frame in a radially outward direction.

2. A method of removing the stent graft device of claim 1 from a lumen, said method comprising:
   applying a mechanical force to said anchoring member to remove said anchoring member from said stent graft device along said removal path.

3. The method of claim 2, further comprising removing said stent graft device from said lumen.

4. A method of removing the stent graft device of claim 1 from a lumen, said method comprising:
   applying a mechanical force to change a geometry of said anchoring member to remove said anchoring member from along a removal path defined by said anchoring member.

5. The method of claim 4, further comprising removing said stent graft device from said lumen.

6. The method of claim 4, wherein said anchoring member is a coiled wire and said changing said geometry comprises uncoiling said anchoring member.

7. The stent graft device of claim 1, wherein raised portions of the anchoring member are spaced away from an outer surface of the expandable frame.

8. A stent graft device comprising:
   an expandable frame configured to transition from a collapsed configuration to an expanded configuration;
   a covering extending over said expandable frame; and
   an anchoring member having a first end and a second end, the anchoring member coupled to said expandable frame by a plurality of coupling members positioned on the exterior surface of said expandable frame and configured to extend along a length of said expandable frame in both the collapsed configuration to the expanded configuration, the anchoring member being configured to adopt a shape when the expandable frame is in the expanded configuration, the shape defining a removal path,
   wherein said shape which said anchoring member is configured to be removed along the removal path while the expandable frame is in the expanded configuration with minimal trauma to any tissue growth over said anchoring member, wherein at least one of the first end and the second end of the anchoring member traverses the removal path and the anchoring member and the removal path are positioned entirely exterior of the covering and the expandable frame.

9. The stent graft device of claim 8, wherein said anchoring member is a wire.

10. The stent graft device of claim 8, wherein the anchoring member is removable upon application of a longitudinal force to the anchoring member.

11. The stent graft device of claim 8, wherein raised portions of the anchoring member are spaced away from an outer surface of the expandable frame.

12. A stent graft device comprising:
   an expandable frame;
   a covering extending over said expandable frame; and
   an anchoring member coupled to said expandable frame by a plurality of coupling members positioned on the exterior surface of said expandable frame and configured to extend along a length of said expandable frame when said expandable frame is in an implanted state, said anchoring member being configured to adopt a shape when said expandable frame is in the implanted state, wherein the adopted shape defines a removal path of said anchoring member,
   wherein said shape which said anchoring member is adapted for removal from said expandable frame along said removal path when the expandable frame is in an expanded configuration so that at least one of the first end and the second end traverse the removal path, wherein the anchoring member and the removal path are positioned entirely exterior of the covering and the expandable frame.

13. The stent graft device of claim 12, wherein said anchoring member is a coiled wire extending outwardly from said expandable support frame in an implanted state, and
   wherein said anchoring member assumes an uncoiled configuration for removal of said stent graft device from said lumen.

14. The stent graft device of claim 12, wherein said anchoring member is a wire.

15. A stent graft device comprising:
   an expandable support frame having incorporated therein an anchoring member coupled to an exterior surface of said expandable frame by a plurality of coupling members positioned on the exterior surface of said expandable frame, the anchor member having a first end and a second end and being configured to adopt a shape when the expandable support frame is in an expanded configuration to anchor said stent graft device in a lumen, the shape defining a removal path; and
   a covering extending over said expandable support frame,
   said anchoring member being removable along said removal path while the expandable frame is in the expanded configuration so that at least one of the first end and the second end traverse the removal path, wherein the anchoring member and the removal path are positioned entirely exterior of the covering and the expandable frame.

16. The stent graft device of claim 15, wherein said anchoring member is a wire.

\* \* \* \* \*